US006653075B2

(12) United States Patent
Tugendreich et al.

(10) Patent No.: US 6,653,075 B2
(45) Date of Patent: Nov. 25, 2003

(54) RANDOM DOMAIN MAPPING

(75) Inventors: Stuart Tugendreich, Mountain View, CA (US); Fernando J. Rebelo Do Couto, Pleasanton, CA (US)

(73) Assignee: Iconix Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 09/738,876

(22) Filed: Dec. 15, 2000

(65) Prior Publication Data

US 2002/0009710 A1 Jan. 24, 2002

Related U.S. Application Data

(60) Provisional application No. 60/172,347, filed on Dec. 16, 1999.

(51) Int. Cl.[7] .............................. C12Q 1/68; C12Q 1/70; C12P 21/06; C12N 9/00; C07H 21/02
(52) U.S. Cl. ................. 435/6; 435/4; 435/183; 435/69.1; 536/23.1; 536/23.2
(58) Field of Search ................. 435/6, 4, 183, 435/69.1; 536/23.1, 23.2

(56) References Cited

U.S. PATENT DOCUMENTS 5,939,250 A * 8/1999 Short ........................... 435/4

FOREIGN PATENT DOCUMENTS

| WO | WO 93/01285 | 1/1993 |
|----|-------------|--------|
| WO | WO 93/15769 | 8/1993 |
| WO | WO 96/23075 | 8/1996 |
| WO | WO 98/32880 | 7/1998 |
| WO | WO 98/39483 | 9/1998 |
| WO | WO 99/24563 | 5/1999 |
| WO | WO 99/31277 | 6/1999 |
| WO | WO 99/38961 | 8/1999 |
| WO | WO 99/53098 | 10/1999 |

OTHER PUBLICATIONS

Jenkins et al., Activating point mutations in the common beta subunit of the human GM–CSF, IL–3 and IL–5 receptors suggest the involvement of beta . . . , 1995, The Embo Journal, vol. 14, pp. 4276–4287.*

Schmidbauer et al., Rapid purification of histidine–tagged glutathione s–transferase fusion protein by metal chelate poros . . . , 1997, Frontiers in Bioscience, vol. 2, pp. c6–8.*

Hegemann et al., A fast method to diagnose chromosome and plasmid loss in *saccharomyces cerevisiae* strains, 1999, Yeast, vol. 15, pp. 1009–1019.*

* cited by examiner

*Primary Examiner*—James Ketter
*Assistant Examiner*—Konstantina Katcheves
(74) *Attorney, Agent, or Firm*—Cooley Godward LLP

(57) ABSTRACT

A method for identifying a mutation-sensitive active region of a test protein, by providing a test nucleic acid construct comprising a regulatable promoter polynucleotide and a fusion polynucleotide comprising a test polynucleotide encoding the test protein fused to a reporter gene, wherein said fusion polynucleotide is operably associated with the promoter polynucleotide, wherein expression of the fusion polynucleotide in a selected host cell results in a specific phenotype and the presence of the reporter; mutagenizing the test nucleic acid construct to provide a mutagenized construct; transforming a selected host cell with the mutagenized construct to provide a transformed host cell; selecting a transformed host cell that exhibits the reporter, but which does not exhibit the specific phenotype; and sequencing a portion of the mutagenized construct from the selected transformed host cell to determine the alteration of the polynucleotide(s). The sequenced polynucleotides will exhibit alterations in one or more critical regions.

20 Claims, No Drawings

RANDOM DOMAIN MAPPING

CROSS-REFERENCE TO RELATED APPLICATION

This application is related to provisional patent application Ser. No. 60/172,347, filed Dec. 16, 1999, from which priority is claimed under 35 USC §119(e)(1) and which is incorporated herein by reference in its entirety.

FIELD OF THE INVENTION

This invention relates generally to the field of molecular biology. More particularly, the invention relates to methods and constructs useful for identifying important and/or essential regions of a protein, whether or not the function or activity of the protein is already known.

BACKGROUND OF THE INVENTION

Current technology enables one to sequence vast amounts of nucleic acids at high speed. However, sequencing alone does not describe the activity of any of the genes sequenced. One can make predictions based on sequence homology that a given gene encodes a protein that exhibits immunoglobulin folds, or may have kinase activity, and the like, but one is limited to identifying features common to known proteins.

If a protein has a known or demonstrable activity, and is not too toxic to express, one can conduct mutagenesis experiments to determine which portion or portions of the protein are responsible for its activity. In general, one prepares a series of mutant versions of the protein in question, typically by a technique such as site-specific mutagenesis, and compares the activity of the mutants with that of the wild type protein. Mutants in which the active portion of the molecule is absent are expected to exhibit little or no activity, while mutants in which an irrelevant part of the molecule is altered are expected to exhibit little difference from the wild type. Due to the number of mutagenesis steps required, one generally selects a few likely spots in the sequence to experiment with, and rarely seeks to alter every residue in turn. Thus, the approach is both time-consuming and incomplete.

SUMMARY OF THE INVENTION

We have now invented a method for systematically and quickly examining substantially every position of a protein sequence, and determining whether or not it is essential to the activity of the protein. The method is effective even if the protein has no known activity, and/or is too toxic to express in its active form.

One aspect of the invention is a method for identifying a mutation-sensitive active region of a test protein, by providing a test nucleic acid construct comprising a regulatable promoter polynucleotide and a fusion polynucleotide comprising a test polynucleotide encoding the test protein fused to a reporter polynucleotide encoding a detectable label, wherein said fusion polynucleotide is operably associated with the promoter polynucleotide, wherein expression of the fusion polynucleotide in a selected host cell results in a specific phenotype and the presence of the detectable label; mutagenizing the test nucleic acid construct to provide a mutagenized construct; transforming a selected host cell with the mutagenized construct to provide a transformed host cell; selecting a transformed host cell that exhibits the detectable label, but which does not exhibit the specific phenotype; and sequencing a portion of the mutagenized construct from the selected transformed host cell to determine the alteration of the polynucleotide(s).

Another aspect of the invention is a population of host cells, comprising a plurality of host cells, each host cell having a test nucleic acid construct which comprises a regulatable promoter polynucleotide and a fusion polynucleotide comprising a mutagenized test polynucleotide encoding a mutagenized test protein fused to a reporter gene encoding a detectable label, wherein the fusion polynucleotide is operably associated with the promoter polynucleotide, and expression of the fusion polynucleotide in the host cell results in expression of said detectable label, wherein the plurality of host cells comprises a plurality of different mutagenized test polynucleotides.

DETAILED DESCRIPTION

Definitions

The term "reporter gene" refers to a polynucleotide that encodes a molecule that can be detected readily, either directly or by its effect on host cell characteristics. Exemplary reporter genes encode enzymes, for example β-galactosidase and URA3, luminescent or fluorescent proteins, such as Green Fluorescent Protein (GFP) and variants thereof, antigenic epitopes (for example Histidine-tag or influenza hemagluttinin tag), mRNA of distinct sequences, and the like. The term "detectable label" refers to a reporter gene or protein that can be detected directly by visual, optical, or spectroscopic methods, such as, for example, GFP, GFP variants, pigments, chromogenic enzymes such as horseradish peroxidase and β-galactosidase, and the like. The terms "selectable label" and "selectable marker" refers to an enzyme reporter gene or protein that facilitates separation of cells that express the label from cells that do not express the label, or to separate cells that express the label to different degrees. Such separation can be by any convenient means, such as, for example, survival of one group or the other, dependence upon a selected nutrient or lack thereof, sensitivity to a given compound, adherence to a solid surface, and the like.

The term "regulatable promoter" refers to a portion of a polynucleotide that is capable of controlling the transcription of nearby DNA, and that responds to the presence or activity of one or more proteins by increasing or decreasing transcription of the affected DNA. A variety of suitable promoters are known, for example GAL, TET, hybrid promoters, and the like.

The term "specific phenotype" as used herein refers to an alteration in one or more characteristics of the host cell distinct from the label, as a result of the heterologous gene or protein presence, for example, death, survival (in the presence of normally lethal conditions or agents), adherence or lack of adherence, morphology, color and appearance, and the like. The specific phenotype excludes any characteristic conferred by the label, which is independent of the specific phenotype: the specific phenotype is preferably observable regardless of the presence or absence of the detectable label as a fusion partner.

The term "mutagenizing" refers to a process for altering the nucleotide sequence of a polynucleotide, for example using PCR, radiation, chemical agents, enzymes, and the like.

The term "fluorescent protein" refers to a protein capable of fluorescing when illuminated. Exemplary fluorescent proteins include, without limitation, the *Aequorea victoria* "Green Fluorescent Protein" ("GFP": see for example D. C. Prasher et al., *Gene* (1992) 111:229–33; M. Chalfie et al., *Science* (1994) 263:802–05, both incorporated herein by reference), and fluorescent mutants thereof ("GFP variants": see for example U.S. Pat. No. 5,625,048 and U.S. 5,777,079, both incorporated herein by reference).

The term "different host cells" refers to a group of host cells that differ genetically from each other. The host cells can be derived from different species (for example, different species of yeast, or different species of mammals), different strains (for example, yeast strains that differ from each other in their genotype but are otherwise derived from the same species, or yeast strains derived by mutagenizing one or more parent strains), different tissue types (for example, human liver cells, fibroblasts, kidney cells, lung cells, tumor cells of various types, and the like), different stages of differentiation, and the like.

General Method

Methods of the invention permit one to quickly identify regions of a protein, for example an enzyme, that are sensitive to mutation. Loss of activity following mutation of one or a few base pairs in a gene suggests that the codon affected encodes an amino acid critical for activity of the encoded protein. This loss of activity may result, for example, from mutation of an active site residue in an enzyme, or from distortion or blocking of a binding site. The resulting information suggests that the affected amino acid can be useful as the target of further drug discovery investigation.

In the practice of the subject method, a host cell is selected for the test nucleic acid such that expression of the test nucleic acid results in a heterologous protein that confers an observable phenotype in the host cell that is due to the heterologous protein activity. For example, expression of the test nucleic acid can be toxic, inhibit host cell growth, alter cell adhesion to a solid support, render the cell reliant on or free from reliance on particular nutrients in its culture media, and the like. The host cell can be any suitable eukaryotic cell, for example yeast, mammalian cells, insect cells, and the like, and can comprise a plurality of cells having different genotypes. For example, one can transform a population of different host cells, for example yeast strains that differ by each having a different gene, signal or metabolic pathway deleted or disabled. The test nucleic acid can be expressed under the control of a regulatable promoter, permitting one to grow the host cell to sufficient density (i.e. by first growing the cells with the regulated promoter turned "off"). If the selected host cell(s) does not display an observable pheno-type in reaction to the test nucleic acid expression, one can select a different host cell, or alter ("sensitize" or potentiate) the selected host cell to render it more sensitive. The host cell can be sensitized by disabling metabolic or signal pathways, or otherwise altering its homeostasis until the cell is rendered dependent upon a pathway that is affected by the heterologous protein. This can be accomplished by standard mutagenesis techniques, generating a mutagenized population of cells and selecting for cells that meet the desired criteria.

The test nucleic acid is then transferred to a vector (such as a plasmid) and placed under the control of a regulatable promoter, and fused with a reporter gene. The reporter gene is preferably positioned downstream of the test nucleic acid, such that reporter gene transcription occurs only after test nucleic acid transcription. The reporter gene is fused to the test nucleic acid in frame, preferably without an intervening stop codon, and is selected so that the resulting heterologous polypeptide/reporter gene product fusion protein still exhibits the biological activity of the heterologous polypeptide and the reporter alone. A presently preferred reporter protein is Green Fluorescent Protein (GFP), and its several variations (collectively "GFPs": see for example, U.S. Pat. Nos. 5,998,204; U.S. 5,998,136; U.S. 5,994,077; U.S. 5,993,778; U.S. 5,985,577; U.S. 5,981,200; and U.S. 5,968,750, all incorporated herein by reference in full). For the rare case in which GFPs interfere with the heterologous protein activity, one can substitute another indicator, such as an epitope tag (an oligopeptide capable of recognition by a specific antibody, typically a unique monoclonal antibody developed specifically to bind to the selected epitope).

The vector is then recovered from the host cell and mutagenized, preferably in an alternate host (for example, *E. coli*), or in vitro. It is possible to mutagenize the vector while in the original host, but this is not preferred due to the introduction of background noise (mutations in other parts of the host genome). One can employ any desired method of mutagenesis: it is presently preferred to randomly mutagenize the vector, for example by chemical and/or radiation means. One can also employ enzymatic methods, for example using "low fidelity" replicases or mutagenizing PCR. Additionally, one can employ combinations of methods, or two or more methods in succession, to obtain the desired degree of mutagenesis. The goal is to attain a level of mutagenesis such that most of the vectors in a population contain one or two point mutations in the target nucleic acid.

The mutagenized vectors are transformed into selected host cells, and the promoters induced to provide expression of the heterologous polypeptide/reporter fusion protein. The transformants are cultured, and are screened for colonies which lack the observable phenotype conferred by the heterologous protein (for example, survival) and exhibit the indicator. For example, where the observable phenotype is death, colonies that exhibit the reporter and survive promoter induction under conditions lethal to control host cells bearing the non-mutagenized vector, must bear a vector having a point mutation in the test nucleic acid that results in a heterologous protein lacking the lethal activity. The vectors are recovered from a plurality of surviving colonies, and the regions of the test nucleic acid that were mutagenized are determined, for example by sequencing. The positions of point mutations indicate which regions of the sequence encode critical residues in the heterologous protein. If a sufficiently large number of vectors are mutagenized, essentially all critical sites (or sites that are sensitive to point mutations) will be indicated by sequence alterations in one or more isolates. Point mutations in regions that do not encode critical residues result in active heterologous protein, and are selected against. Thus, a histogram of the number of mutations for each amino acid residue in the heterologous protein will show one or more mutations at positions where mutation of the residue substantially alters activity, and will show few if any mutations at positions that are not sensitive to mutation. An experiment of sufficient size (sufficiently large number of mutants) will unequivocally indicate the "critical" portions of a protein, including its active sites and/or binding sites, thus pointing out relevant targets for the design of pharmaceutical agents.

A slightly altered method of the above involves first mutagenizing the test nucleic acid (by mutagenic PCR for example) and placing it into the promoter/reporter vector (by recombination for example) and into the recipient cells in a single step. This alternative method allows one to enhance the targeting of the mutations to the test nucleic acid, because only the test nucleic acid is exposed to the mutagenic conditions.

EXAMPLES

The following examples are provided as a guide for the practitioner of ordinary skill in the art. Nothing in the examples is intended to limit the claimed invention. Unless otherwise specified, all reagents are used in accordance with the manufacturer's recommendations, and all reactions are performed at standard temperature and pressure.

Example 1

A yeast host strain EIS20 was constructed by integrating a vector providing a GAL promoter regulating expression of the test gene fused to GFP, KanMX, and LEU2. When grown on GAL media, expression of the zinc-finger type DNA binding protein encoded by the test gene was lethal to the host cells.

A transfer plasmid was constructed in plasmid pARC33B having the GAL promoter upstream of a GFP gene, and also containing HIS3 and CEN. The transfer plasmid was digested with SphI and Hinc II, cleaving the plasmid upstream of the GAL promoter and within the GFP gene, and transformed into the host strain. The digested transfer plasmid recombines with the integrated DNA to form a new transfer vector containing the test gene fused to GFP, under control of the GAL promoter. This new vector was rescued into E. coli.

The rescued vector was isolated using a Qiagen prep, and an aliquot of the purified plasmid (4 μg) mutagenized by exposure to hydroxylamine (200 μl, 75° C., 1 M $HONH_2$, 2 mM EDTA, 100 mM NaCl, 50 mM sodium pyrophosphate), with 20 μl aliquots drawn at 0, 5, 10, 15, 20, 30, 60, and 90 minutes, then transformed into naive host cells (lacking the non-mutagenized heterologous gene integration). Half of the transformed hosts were induced by plating on His synthetic complete media (0% his, 2% glucose,) to select for hosts containing the plasmid. The number of colonies obtained varied with exposure time to hydroxylamine, as expected:

TABLE 1

Number of colonies on HIS-selective media vs. mutagenesis time

| Exposure Time (min) | Number of colonies |
|---|---|
| 0 | 5000 |
| 5 | 5000 |
| 10 | 3000 |
| 15 | 2000 |
| 20 | 1000 |
| 30 | 20 |
| 60 | 0 |
| 90 | 0 |

The other half of the host cells were cultured on SC-His+ Gal plates (0% his, 2% galactose, 0.005% glucose, 0.005% extra adenine), simultaneously selecting against cells lacking the plasmid, and inducing expression of the fusion protein (test gene-GFP). This resulted in a set of cultures (colonies) exhibiting GFP fluorescence, and a set that failed to fluoresce:

TABLE 2

Number of fluorescent and non-fluorescent colonies on inducing media as a function of mutagenesis time

| Exposure Time (min) | Total Colonies | GFP Colonies |
|---|---|---|
| 0 | 0 | 0 |
| 5 | 85 | 49 |
| 10 | 132 | 69 |
| 15 | 98 | 58 |
| 20 | 40 | 20 |
| 30 | 5 | 2 |
| 60 | 0 | 0 |
| 90 | 0 | 0 |

These results demonstrate that some of the plasmids carry mutations in the test gene sequence that abrogate its toxicity (indicated by the colonies that exhibit GFP fluorescence), along with other plasmids which fail to fluoresce due to mutations in the promoter or the GFP gene, introduction of a stop codon in the test gene or GFP sequences, or a combination thereof. Mutations that fail to alter the test gene activity (e.g., silent mutations, or mutations that affect non-essential amino acids) do not result in viable colonies.

A number of colonies were sequenced to determine the location of the point mutations. Of 18 fluorescent colonies sequenced, 16 of the point mutations occurred in either of two zinc finger motifs, with only four point mutations occurring outside the two zinc finger domains (two of which belonged to double-mutant sequences, each having a second mutation within the zinc finger domain). Seven non-fluorescent colonies were also sequenced: in each case, a point mutation had resulted in substitution of a stop codon, effectively truncating the heterologous protein.

What is claimed:

1. A method for identifying a mutation-sensitive active region of a test protein, said method comprising:
   a) providing a test nucleic acid construct comprising
      (i) a regulatable promoter polynucleotide; and
      (ii) a fusion polynucleotide comprising a test polynucleotide encoding said test protein fused to a reporter gene encoding a detectable label, wherein said fusion polynucleotide is operably associated with said promoter polynucleotide, wherein expression of said fusion polynucleotide in a selected host cell results in a specific phenotype dependent upon said test protein and distinct from said detectable label, and the presence of said detectable label;
   b) mutagenizing said test nucleic acid construct to provide a mutagenized construct comprising a mutagenized fusion polynucleotide;
   c) transforming a selected host cell with said mutagenized construct to provide a transformed host cell;
   d) inducing expression of said mutagenized construct;
   e) selecting a transformed host cell that exhibits said detectable label, but which does not exhibit said specific phenotype; and
   f) sequencing a portion of said mutagenized construct from said selected transformed host cell to determine which polynucleotide(s) was altered.

2. The method of claim 1, wherein said specific phenotype is selected from the group consisting of growth inhibition and survival.

3. The method of claim 1, wherein said reporter gene encodes GFP or a GFP variant.

4. The method of claim 1, wherein said reporter gene comprises URA3.

5. The method of claim 1, wherein said mutagenized construct further comprises a selectable marker.

6. The method of claim 5, wherein said selectable marker comprises a Histidine tag.

7. The method of claim 1, further comprising integrating said mutagenized fusion polynucleotide into the genome of said host cell.

8. A population of test cells, comprising:
   a) a plurality of host cells, each host cell comprising a test nucleic acid construct which comprises
      (i) a regulatable promoter polynucleotide; and
      (ii) a fusion polynucleotide comprising a mutagenized test polynucleotide encoding a mutagenized test protein fused to a reporter gene encoding a detectable label, wherein said fusion polynucleotide is operably associated with said promoter polynucleotide, wherein expression of said fusion polynucleotide in said host cell results in expression of said detectable label;
   wherein said plurality of host cells comprises a plurality of different mutagenized test polynucleotides.

9. The population of claim 8, wherein said detectable label comprises GFP or a GFP variant.

10. The population of claim 8, wherein said host cell is selected from the group consisting of mammalian cells and yeast.

11. A method for identifying a mutation-sensitive region of a test protein, said method comprising:
   a) providing a test nucleic acid construct comprising
      (i) a regulatable promoter polynucleotide; and
      (ii) a fusion polynucleotide comprising a test polynucleotide encoding said test protein fused to a reporter gene encoding a detectable label, wherein said fusion polynucleotide is operably associated with said promoter polynucleotide,
   b) introducing said test nucleic acid into a plurality of different host cells;
   c) inducing expression of said fusion polynucleotide;
   d) selecting host cells wherein expression of said fusion polynucleotide results in a specific phenotype dependent upon said test protein and distinct from said detectable label, and the presence of said detectable label;
   e) mutagenizing said test nucleic said construct to provide a plurality of mutagenized constructs comprising a plurality of different mutagenized fusion polynucleotides;
   f) transforming a selected host cell with said mutagenized constructs to provide a plurality of transformed host cells;
   g) inducing expression of said mutagenized constructs;
   h) selecting a plurality of transformed host cells that exhibit said detectable label, but which do not exhibit said specific phenotype; and
   i) determining which polynucleotide(s) were altered in a plurality of mutagenized constructs.

12. The method of claim 11, wherein step e) further comprises recovering said test nucleic acid construct from said host cell prior to mutagenizing said test nucleic acid construct.

13. The method of claim 11, wherein said reporter gene encodes a fluorescent protein.

14. The method of claim 11, wherein said reporter gene comprises URA3.

15. The method of claim 11, wherein said mutagenized construct further comprises a selectable label.

16. The method of claim 11, wherein said plurality of different host cells comprises a plurality of different yeast strains.

17. The method of claim 11, wherein said plurality of different host cells comprises a plurality of different mammalian cell types.

18. The method of claim 11, wherein said plurality of different host cells comprises a plurality of yeast strains obtained by mutagenesis.

19. The method of claim 11, wherein said plurality of different host cells comprises a plurality of cell lines derived from different tissue types.

20. The method of claim 19, wherein said host cells are human cells.

* * * * *